United States Patent [19]

Hashimoto et al.

[11] Patent Number: 5,252,750

[45] Date of Patent: Oct. 12, 1993

[54] POLYOLEFIN AMINO DERIVATIVES

[75] Inventors: Mitsuru Hashimoto; Tomoyuki Shimada, both of Numazu; Nobuo Suzuki, Kouriyama; Takayuki Sakai, Tokyo; Susumu Suzuka, Yono; Masaomi Sasaki, Susono, all of Japan

[73] Assignees: Ricoh Company, Ltd.; Hodogaya Chemical Company, Ltd., both of Tokyo, Japan

[21] Appl. No.: 709,294

[22] Filed: Jun. 3, 1991

Related U.S. Application Data

[62] Division of Ser. No. 562,623, Aug. 3, 1990, Pat. No. 5,068,350, which is a division of Ser. No. 245,288, Sep. 16, 1988, Pat. No. 4,965,157.

[30] Foreign Application Priority Data

| Sep. 17, 1987 | [JP] | Japan | 62-232894 |
| Sep. 17, 1987 | [JP] | Japan | 62-232895 |
| May 27, 1988 | [JP] | Japan | 63-131247 |
| May 27, 1988 | [JP] | Japan | 63-131248 |

[51] Int. Cl.$^5$ .......................... C07C 211/54
[52] U.S. Cl. ...................... 549/59; 549/79; 564/307; 564/391; 564/434

[58] Field of Search .............. 564/307, 391, 434; 549/59, 74

[56] References Cited

U.S. PATENT DOCUMENTS 4,912,259 3/1990 Kaneko .................. 564/434

OTHER PUBLICATIONS

Somanathan et al., Chemical Abstracts, vol. 99 (1983) 53462c.
Ueda, Chemical Abstracts, vol. 115 (1991) 60832q.

*Primary Examiner*—Richard L. Raymond
*Attorney, Agent, or Firm*—Oblon, Spivak, McClelland, Maier & Neustadt

[57] ABSTRACT

Polyolefin derivatives, which are useful not only as the photoconductive materials for electrophotography, but also as a charge transporting material employed in a function-separating type photoconductor which uses an organic or inorganic pigment as a charge generating material, and an electrophotographic photoconductor containing at least one of the above polyolefin derivatives in a photoconductive layer thereof, are disclosed.

13 Claims, 1 Drawing Sheet

POLYOLEFIN AMINO DERIVATIVES

This is a division of application Ser. No. 07/562,623, filed on Aug. 3, 1990, now U.S. Pat. No. 5,068,350, which is a division of U.S. application Ser. No. 07/245,288, filed Sep. 16, 1998, now U.S. Pat. No. 4,967,157.

BACKGROUND OF THE INVENTION

The present invention relates to polyolefin derivatives, and an electrophotographic photoconductor which comprises a photoconductive layer containing at least one of the polyolefin derivatives.

Examples of photoconductive materials for use in conventional photoconductors for use in electrophotography are selenium, cadmium sulfide, and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made of a polymeric material; thus visible developed images can be obtained on the photoconductor.

Fundamental characteristics required of the photoconductor for use in electrophotography are: (1) chargeability to a predetermined potential in the dark; (2) minimum electric charge dissipation in the dark; and (3) quick dissipation of electric charges upon exposure to light.

While the above-mentioned inorganic photoconductive materials have many advantages over other conventional photoconductive materials, they also have several shortcomings.

For example, a selenium photoconductor, which is widely used at present and sufficiently meets the above-mentioned requirements (1) to (3), has the shortcomings that its production conditions are difficult and, accordingly, its production cost is high. Further it is difficult to work it into the form of a belt due to its poor flexibility, and it is so vulnerable to heat and mechanical shock that it must be handled with the utmost care.

Cadmium sulfide photoconductors and zinc oxide photoconductors are prepared by dispersing cadmium sulfide or zinc oxide in a binder resin. Therefore they are so poor in mechanical properties such as surface smoothness, hardness, tensile strength and wear resistance that they are not suitable as photoconductors for use in plain paper copiers in which the photoconductors are used in quick repetition.

Recently, varieties of the organic electrophotographic photoconductor have been proposed to cover the shortcomings of the inorganic photoconductor, and some of them are in fact put to practical use. Representative examples of the organic electrophotographic photoconductor are an electrophotographic photoconductor comprising poly-N-vinylcarbazole and 2,4,7-trinitro-fluorene-9-one (U.S. Pat. No. 3,484,237), a photoconductor in which poly-N-vinylcarbazole is sensitized by a pyrylium salt type dyestuff (Japanese Patent Publication 48-25658), a photoconductor containing as the main component an organic pigment (Japanese Laid-Open Patent Application 47-37543), and a photoconductor containing as the main component an eutectic crystalline complex made of a dye and a resin (Japanese Laid-Open Patent Application 47-10735).

Although the above-mentioned organic electrophotographic photoconductors have many superiorities for practical use compared with other conventional photoconductors, they do still not satisfy all the requirements of the electrophotographic photoconductor.

SUMMARY OF THE INVENTION

It is therefore an object of the present invention to provide an improved electrophotographic photoconductor, from which the above-mentioned conventional shortcomings are eliminated. More specifically, it is an object of the present invention to provide an electrophotographic photoconductor which is manufactured without difficulty at relatively low cost and shows a good durability.

Another object of the present invention is to provide particular novel polyolefin derivatives which are contained in the photoconductive layer of the electrophotographic photoconductor according to the present invention.

The above first object of the present invention can be attained by an electrophotographic photoconductor in which a photoconductive layer is overlaid on an electroconductive support, which photoconductive layer comprises as an effective component at least one polyolefin derivative having the following formula (I):

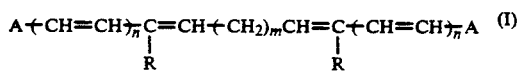

wherein A represents 9-anthryl group, a substituted or unsubstituted N-substituted carbazolyl group, N-substituted phenothiazinyl group, or

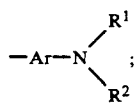

wherein Ar represents a substituted or unsubstituted allylene group, and $R^1$ and $R^2$ each represent a substituted or unsubstituted alkyl group, a substituted or unsubstituted aralkyl group or a substituted or unsubstituted aryl group, R represents hydrogen, a substituted or unsubstituted alkyl group, a substituted or unsubstituted aralkyl group or a substituted or unsubstituted aryl group; m is an integer of 2 to 8; and n is an integer of 0 or 1.

The above polyolefin derivative represented by the formula (I), which polyolefin derivative is contained in the photoconductive layer for use in the present invention, can be prepared by reacting an alkylene derivative having the formula (II) with a carbonyl compound having the formula (III):

wherein Y represents

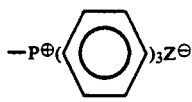

in which $Z^\ominus$ indicates a halogen ion, or $-PO(OR_1)_2$ in which $R_1$ represents a lower alkyl group; and $l$ is an integer of 4 to 10.

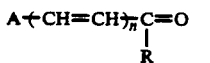

wherein A, R and n are respectively the same as those defined in the above-mentioned general formula (I).

The second object of the present invention can be achieved by the polyolefin derivatives having the general formula (I). Among these polyolefin derivatives, the following polyolefin derivatives represented by the formula (IV) are particularly preferable for practical use.

wherein n is an integer of 2 to 8, and A represents 9-anthryl group, a substituted or unsubstituted N-substituted carbazolyl group, N-alkylphenothiazyl group, or

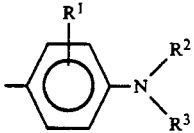

wherein $R^1$ represents halogen, a lower alkyl group or a lower alkoxy group, and $R^2$ and $R^3$ each represent a substituted or unsubstituted alkyl group, provided that $R^2$ and $R^3$ are not a methyl group at the same time when n is an integer of 2; a substituted or unsubstituted aralkyl group; or a substituted or unsubstituted aryl group.

The above preferable polyolefin derivatives having the formula (IV) can be prepared by the same reaction as that described in the polyolefin derivatives represented by the formula (I).

DETAILED DESCRIPTION OF THE PREFERRED EMBODIMENTS

Figure 1:
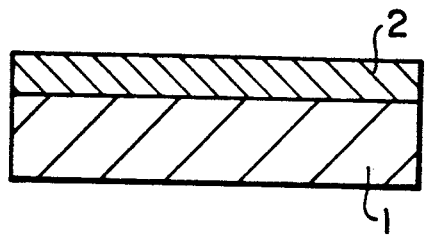
FIG. 1 through FIG. 5 are the enlarged schematic cross-sectional views of an embodiment of an electrophotographic photoconductor according to the present invention.

The polyolefin derivatives having the formula (I) according to the present invention, which are novel materials, can be prepared by reacting an alkylene compound of the formula (II) with an aldehyde compound of the formula (III) in the presence of a basic catalyst.

As the basic catalyst for the above reaction, potassium hydroxide, sodium amide, sodium methylate, and alcoholates such as potassium methylate and potassium-t-butoxide can be employed.

As the reaction solvent, methanol, ethanol, propanol, toluene, xylene, dioxane, N,N-dimethylformamide, dimethyl sulfoxide, and tetrahydrofuran can be used.

The reaction temperature for the above reaction can be set in a relatively wide range, depending upon (1) the stability of the solvent employed in the presence of the basic catalyst, (2) the reactivities of the condensation components, that is, the compound of the formula (II) and the compound of the formula (III), and (3) the reactivity of the basic catalyst in the solvent employed, which catalyst works as a condensation agent in this reaction.

When a polar solvent is, for example, employed as the reaction solvent, the reaction temperature can be set in the range of room temperature to about 100° C., preferably in the range of room temperature to about 80° C. However, if it is desired to shorten the reaction time or when a less reactive condensation agent is employed, the reaction temperature can be elevated beyond the aforementioned range.

The compound having the formula (II), which is allowed to react with the compound (III) to prepare the polyolefin derivatives according to the present invention, can be obtained without difficulty by reacting an alkylene compound, which is halogen-substituted at both ends of its molecule, with trialkyl phosphite or triphenylphosphine, directly or in the organic solvent such as toluene, xylene and N,N'-dimethylformamide with application of heat thereto.

Specific examples of the thus prepared novel polyolefin derivatives according to the present invention are as follows:

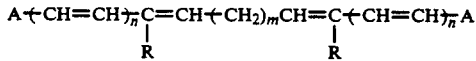

| Derivative No. | A | R | n | m |
|---|---|---|---|---|
| 1 | (N-methylcarbazolyl) | H | 0 | 2 |

-continued
| | | | | |
|---|---|---|---|---|
| 2 | 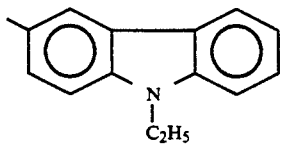 | H | 0 | 2 |
| 3 | 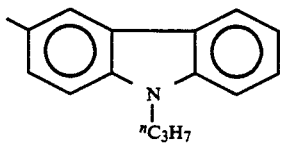 | H | 0 | 2 |
| 4 | 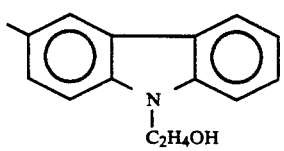 | H | 0 | 2 |
| 5 | 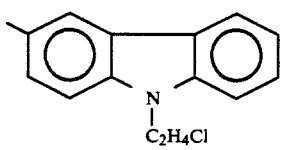 | H | 0 | 2 |
| 6 | 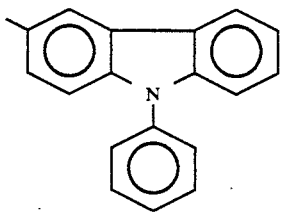 | H | 0 | 2 |
| 7 | 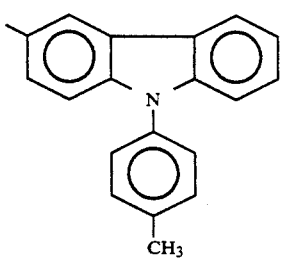 | H | 0 | 2 |
| 8 | 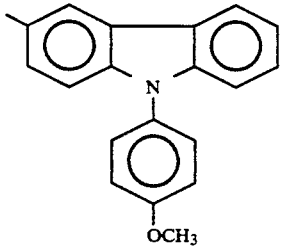 | H | 0 | 2 |
| 9 | 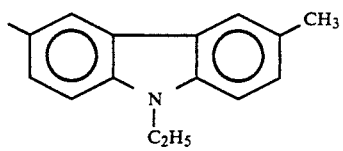 | H | 0 | 2 |

-continued
| | | | | | |
|---|---|---|---|---|---|
| 10 | 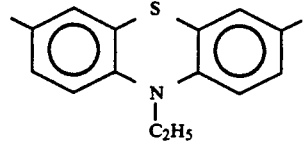 | H | 0 | 2 |
| 11 | 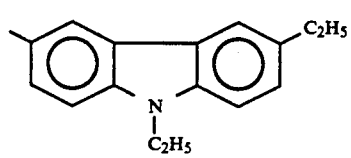 | H | 0 | 2 |
| 12 | 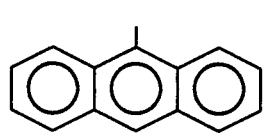 | H | 0 | 2 |
| 13 | 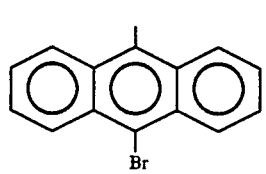 | H | 0 | 2 |
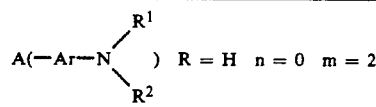  R = H  n = 0  m = 2
| Derivative No. | Ar | R¹ | R² |
|---|---|---|---|
| 14 | 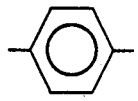 | —CH₃ | —CH₃ |
| 15 | 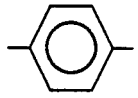 | —C₂H₅ | —C₂H₅ |
| 16 | 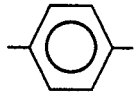 | —CH₃ | 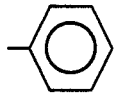 |
| 17 |  | —C₂H₅ | 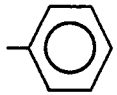 |
| 18 |  | 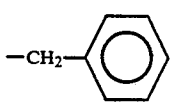 | 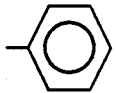 |
| 19 |  | 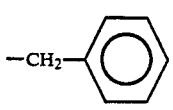 | 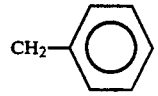 |
| 20 |  | 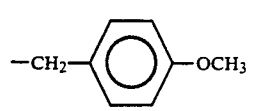 | 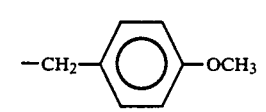 |

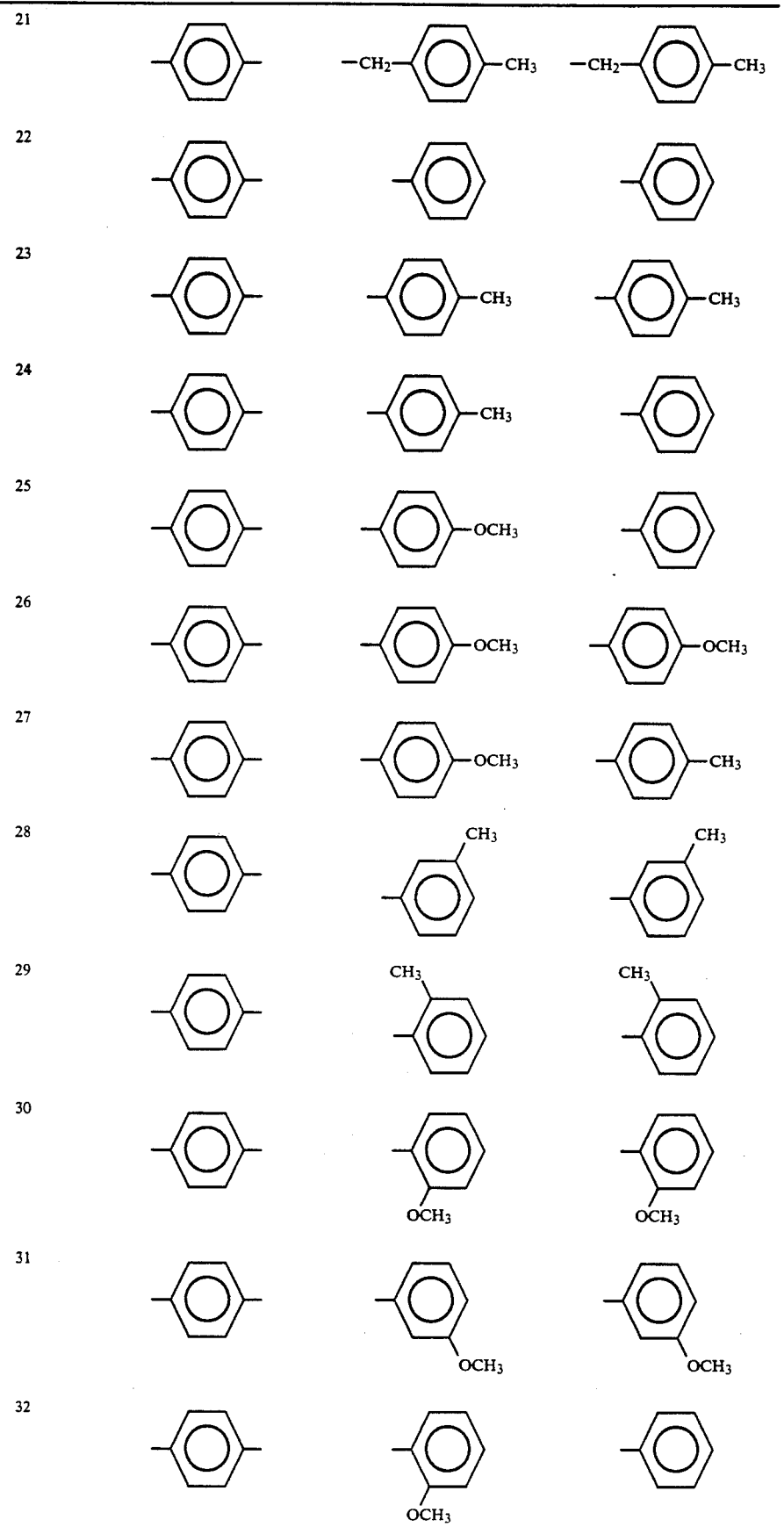

-continued
| | | | |
|---|---|---|---|
| 33 | 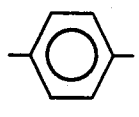 | 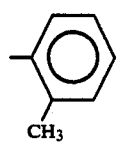 | 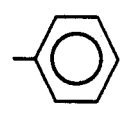 |
| 34 | 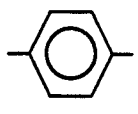 | 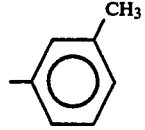 | 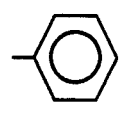 |
| 35 | 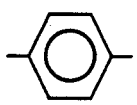 | 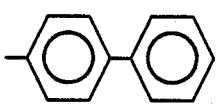 | 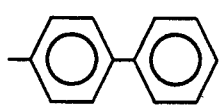 |
| 36 | 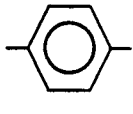 | 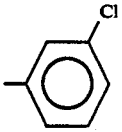 | 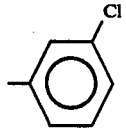 |
| 37 | 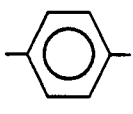 | 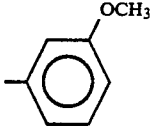 | 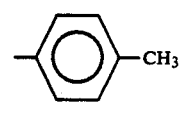 |
| 38 | 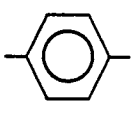 | 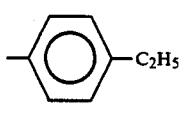 | 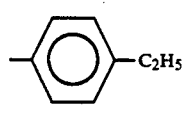 |
| 39 | 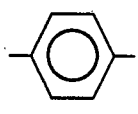 | 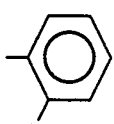 | 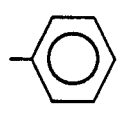 |
| 40 | 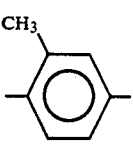 | 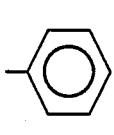 | 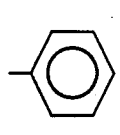 |
| 41 | 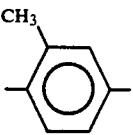 | 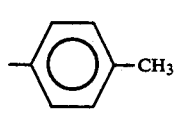 | 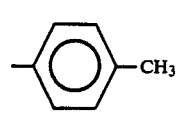 |
| 42 | 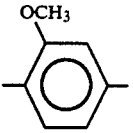 | 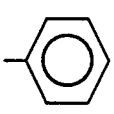 | 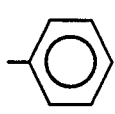 |
| 43 | 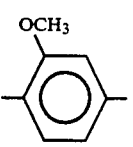 | 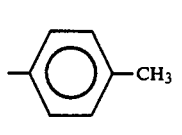 | 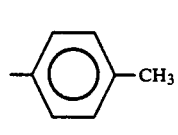 |

-continued
| No. | | | |
|---|---|---|---|
| 44 | 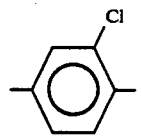 | 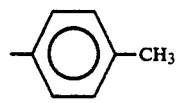 | 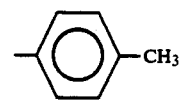 |
| 45 | 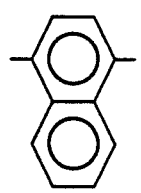 | 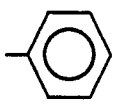 | 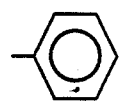 |
| 46 | 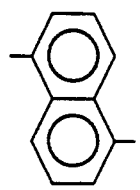 | 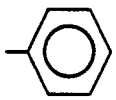 | 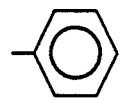 |
| 47 | 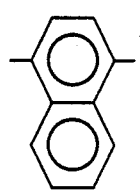 | 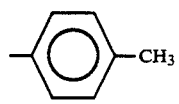 | 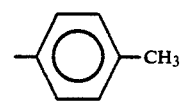 |
| 48 | 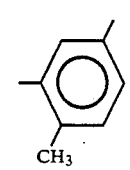 | 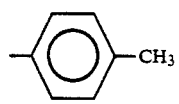 | 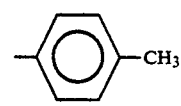 |
| 49 | 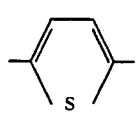 | 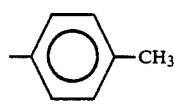 | 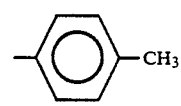 |
| 50 | 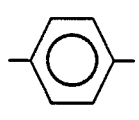 | 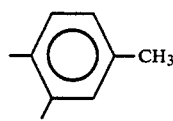 | 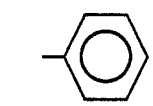 |
| 51 | 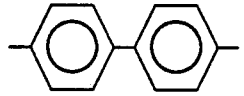 | 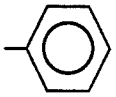 | 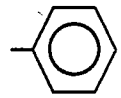 |
| 52 | 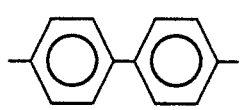 | 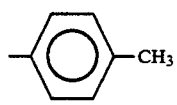 | 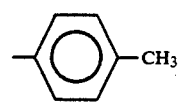 |
| Derivative No. | Ar | $R^1$ | $R^2$ | R | n | m |
|---|---|---|---|---|---|---|
| 53 | 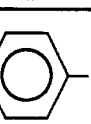 | $CH_3$ | $CH_3$ | H | 1 | 2 |

-continued
| No. | | | | | n | m |
|---|---|---|---|---|---|---|
| 54 | 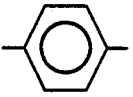 | CH₃ | CH₃ | CH₃ | 0 | 2 |
| 55 |  | CH₃ | CH₃ | 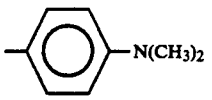—N(CH₃)₂ | 0 | 2 |
| 56 |  | 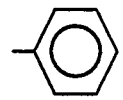 | 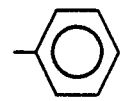 | CH₃ | 0 | 2 |
| 57 |  | 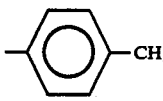—CH₃ | 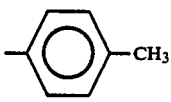—CH₃ | CH₃ | 0 | 2 |
| 58 |  | 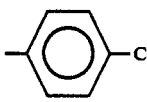—CH₃ | 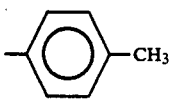—CH₃ | 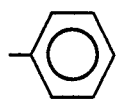 | 0 | 2 |
| 59 |  | 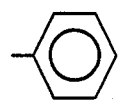 | 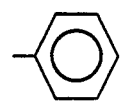 | —CH₂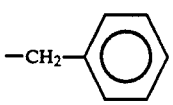 | 0 | 2 |
| 60 | 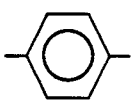 | 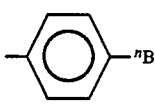—ⁿBu | 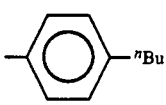—ⁿBu | H | 0 | 2 |
| 61 | 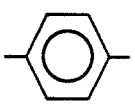 | 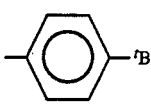—ᵗBu | 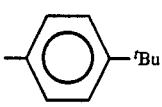—ᵗBu | H | 0 | 2 |
| 62 | 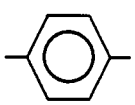 | 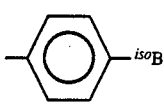—ⁱˢᵒBu | 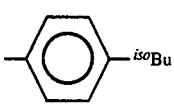—ⁱˢᵒBu | H | 0 | 2 |
| Derivative No. | A | R | n | m |
|---|---|---|---|---|
| 63 | 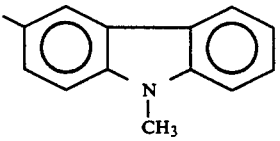 | H | 0 | 3 |
| 64 | 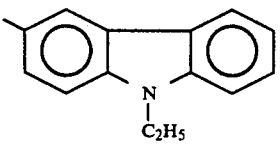 | H | 0 | 3 |
| 65 | 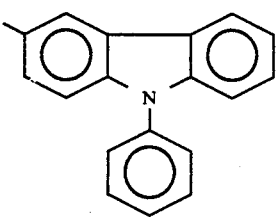 | H | 0 | 4 |

-continued
| | | | | |
|---|---|---|---|---|
| 66 | 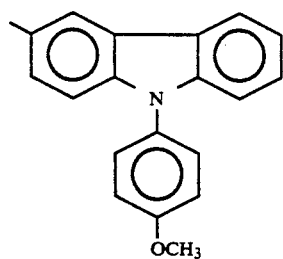 | H | 0 | 4 |
| 67 | 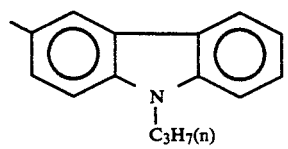 | H | 0 | 4 |
| 68 | 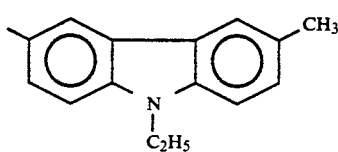 | H | 0 | 4 |
| 69 | 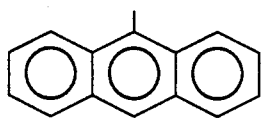 | H | 0 | 3 |
| 70 | 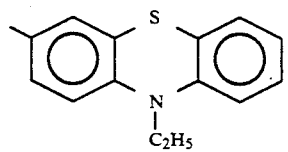 | H | 0 | 3 |
| 71 | 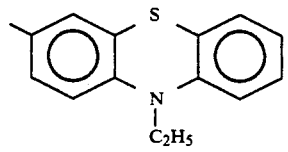 | H | 0 | 4 |
| 72 | 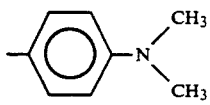 | H | 0 | 3 |
| 73 | 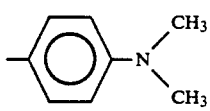 | H | 1 | 3 |
| 74 | 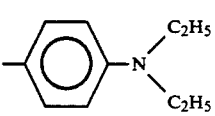 | H | 0 | 3 |
| 75 | 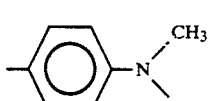 | 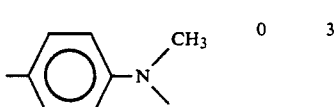 | 0 | 3 |

-continued
| | | | | |
|---|---|---|---|---|
| 76 | 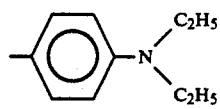 | 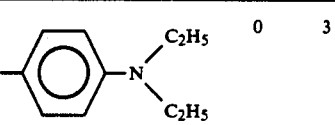 | 0 | 3 |
| 77 | 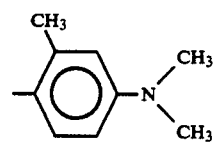 | H | 0 | 5 |
| 78 | 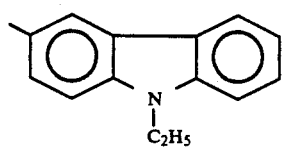 | H | 0 | 8 |
| 79 | 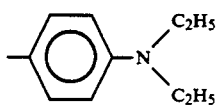 | H | 0 | 6 |
| 80 | 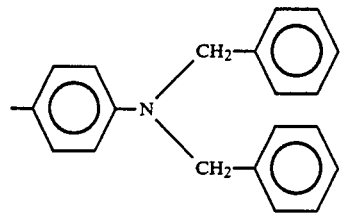 | H | 0 | 3 |
| 81 | " | H | 0 | 4 |
| 82 | " | H | 0 | 8 |
| 83 | 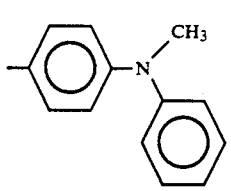 | H | 0 | 4 |
| 84 | 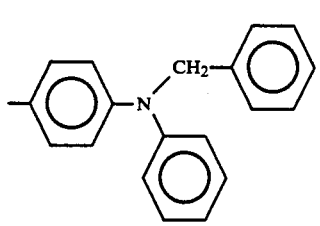 | H | 0 | 4 |
| 85 | 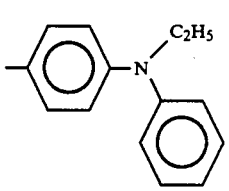 | H | 0 | 3 |

-continued
| | | | | |
|---|---|---|---|---|
| 86 | 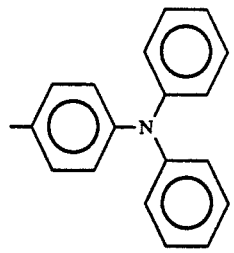 | H | 0 | 3 |
| 87 | " | H | 0 | 4 |
| 88 | " | H | 0 | 5 |
| 89 | " | H | 0 | 6 |
| 90 | " | H | 0 | 7 |
| 91 | " | H | 0 | 8 |
| 92 | 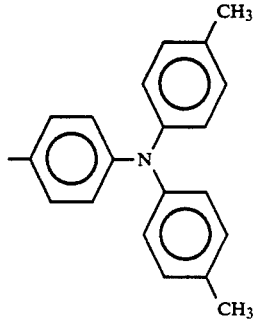 | H | 0 | 3 |
| 93 | " | H | 0 | 4 |
| 94 | " | H | 0 | 5 |
| 95 | " | H | 0 | 6 |
| 96 | " | H | 0 | 7 |
| 97 | " | H | 0 | 8 |
| 98 | 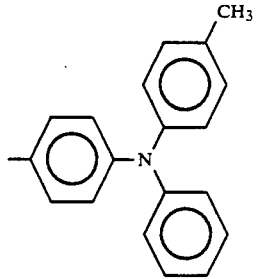 | H | 0 | 3 |
| 99 | 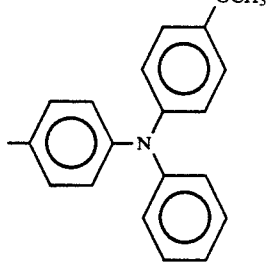 | H | 0 | 8 |
| 100 | 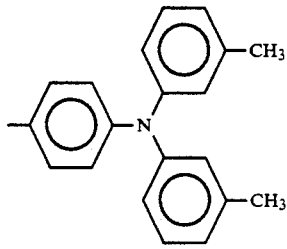 | H | 0 | 3 |

-continued
| | | | | | |
|---|---|---|---|---|---|
| 101 | " | | H | 0 | 4 |
| 102 | " | | H | 0 | 8 |
| 103 | 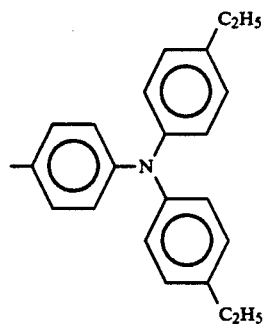 | | H | 0 | 4 |
| 104 | 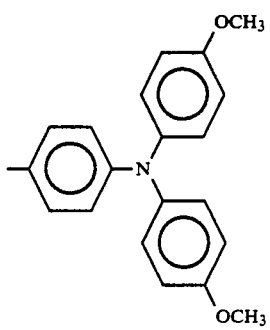 | | H | 0 | 3 |
| 105 | " | | H | 0 | 4 |
| 106 | " | | H | 0 | 8 |
| 107 | 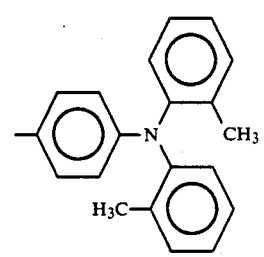 | | H | 0 | 3 |
| 108 | " | | H | 0 | 4 |
| 109 | 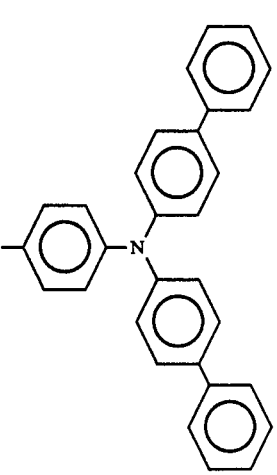 | | H | 0 | 4 |

-continued
| | | | | |
|---|---|---|---|---|
| 110 | 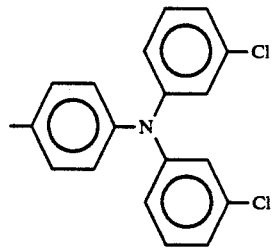 | H | 0 | 3 |
| 111 | 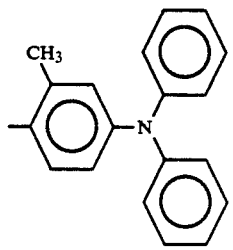 | H | 0 | 3 |
| 112 | 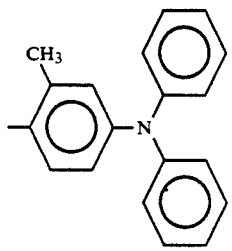 | H | 0 | 4 |
| 113 | " | H | 0 | 8 |
| 114 | 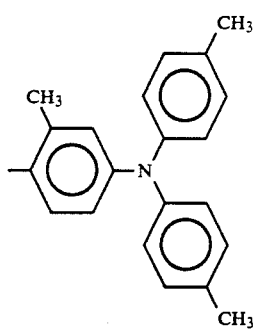 | H | 0 | 3 |
| 115 | " | H | 0 | 4 |
| 116 | " | H | 0 | 5 |
| 117 | " | H | 0 | 6 |
| 118 | 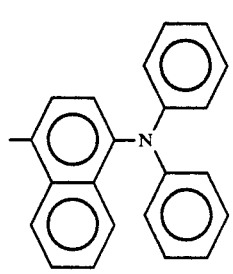 | H | 0 | 3 |

-continued
| | | | | |
|---|---|---|---|---|
| 119 | 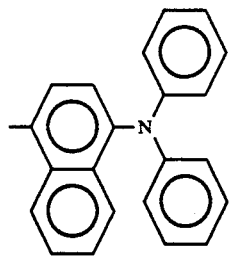 | H | 0 | 4 |
| 120 | " | H | 0 | 8 |
| 121 | 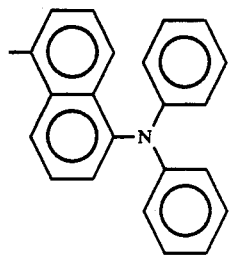 | H | 0 | 3 |
| 122 | " | H | 0 | 4 |
| 123 | " | H | 0 | 8 |
| 124 | 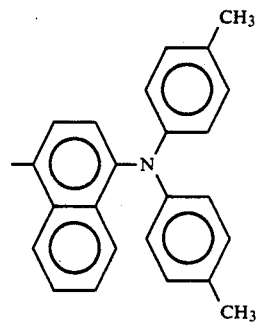 | H | 0 | 3 |
| 125 | " | H | 0 | 4 |
| 126 | 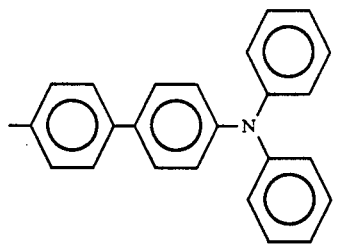 | H | 0 | 3 |
| 127 | " | H | 0 | 4 |
| 128 | " | H | 0 | 8 |
| 129 | 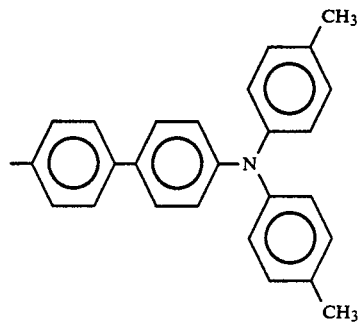 | H | 0 | 3 |

-continued
| | | | | |
|---|---|---|---|---|
| 130 | " | H | 0 | 4 |
| 131 | " | H | 0 | 5 |
| 132 | " | H | 0 | 6 |
| 133 | " | H | 0 | 7 |
| 134 | " | H | 0 | 8 |
| 135 | 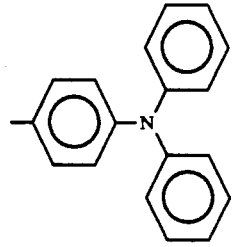 | CH₃ | 0 | 3 |
| 136 | 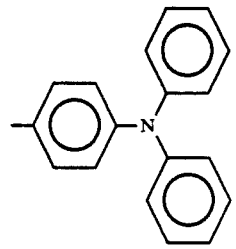 | CH₃ | 0 | 4 |
| 137 | 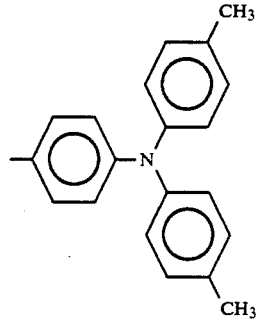 | CH₃ | 0 | 3 |
| 138 | " | CH₃ | 0 | 4 |
| 139 | " | CH₃ | 0 | 8 |
| 140 | 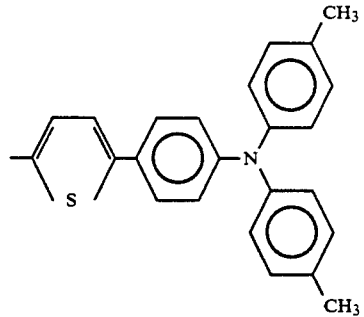 | H | 0 | 3 |
| 141 | 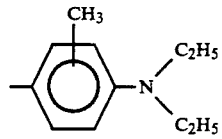 | H | 0 | 2 |
| 142 | 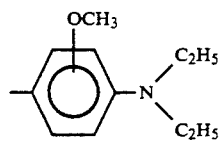 | H | 0 | 2 |

-continued
| | | | | |
|---|---|---|---|---|
| 143 | 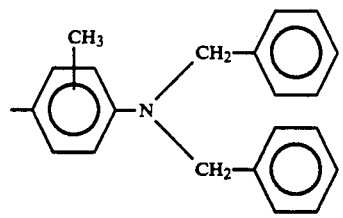 | H | 0 | 2 |
| 144 | 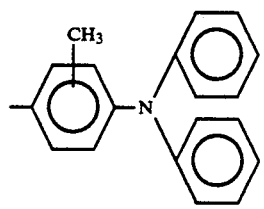 | H | 0 | 2 |
| 145 | 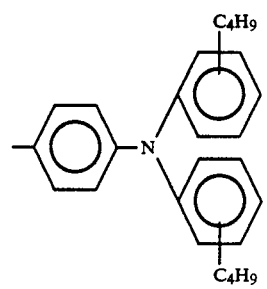 | H | 0 | 2 |
| 146 | 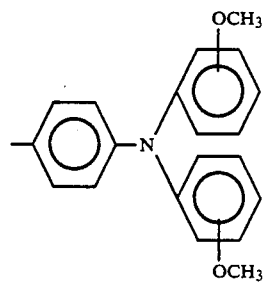 | H | 0 | 2 |
| 147 | 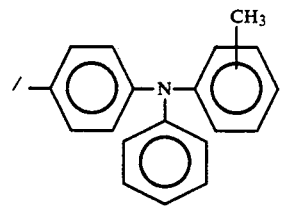 | H | 0 | 2 |
| 148 | 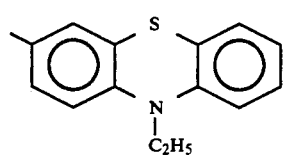 | H | 0 | 2 |
| 149 | 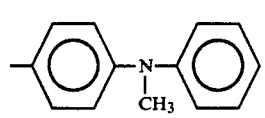 | H | 0 | 2 |

-continued
| | | | | |
|---|---|---|---|---|
| 150 | 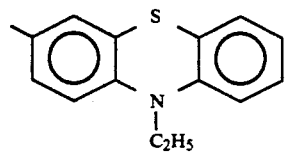 | H | 0 | 6 |
| 151 | 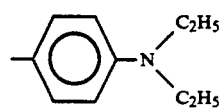 | H | 0 | 3 |
| 152 | 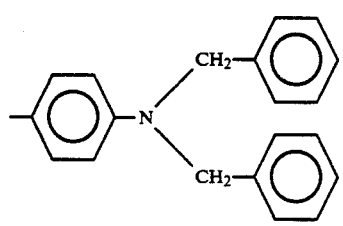 | H | 0 | 4 |
| 153 | 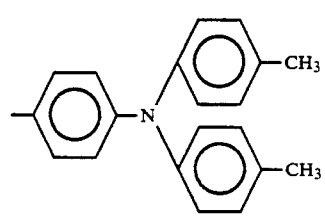 | H | 0 | 6 |
| 154 | 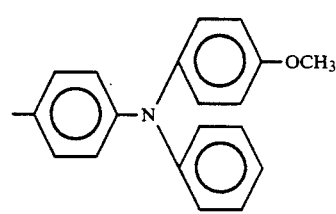 | H | 0 | 8 |
| 155 | 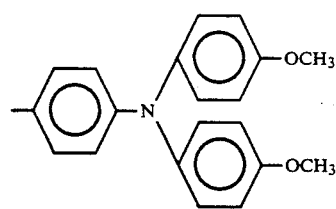 | H | 0 | 4 |
| 156 | 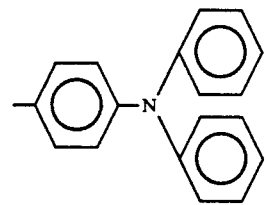 | H | 0 | 8 |
| 157 | 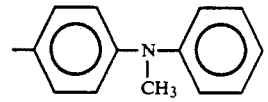 | H | 0 | 4 |

| | | | | |
|---|---|---|---|---|
| 158 | 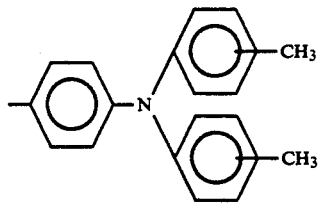 | H | 0 | 4 |
| 159 | 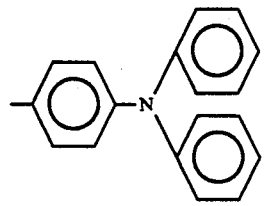 | H | 0 | 4 |
| 160 | 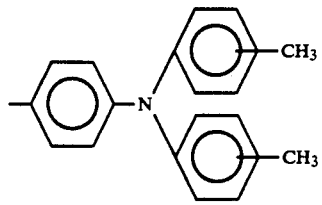 | H | 0 | 3 |
| 161 | 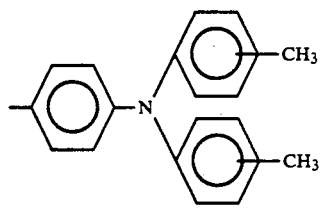 | H | 0 | 8 |
| 162 | 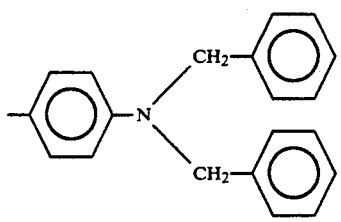 | H | 0 | 3 |

The novel polyolefin derivatives according to the present invention are remarkably useful for the electrophotographic photoconductor as the photoconductive materials. These polyolefin derivatives can be either optically or chemically sensitized by a sensitizer such as dyes and Lewis acids. Furthermore, the above-mentioned polyolefin derivatives are particularly useful as a charge transporting material employed in the so-called function-separating type photoconductor which uses an organic or inorganic pigment as a charge generating material.

The polyolefin derivatives according to the present invention can be advantageously manufactured because their materials are easy to obtain and the reaction to prepare the polyolefin derivatives can be readily induced.

The present invention will now be explained in detail by referring to the following examples.

SYNTHESIS EXAMPLE 1

Synthesis of Polyolefin Derivative No. 23

A mixture of 37.0 g (0.05 mol) of tetramethylene-1,4-bis(triphenylphosphonium)dibromide and 29.1 g (0.105 mol) of 4-(N,N-di-p-tolylamino)benzaldehyde was dissolved in 250 ml of toluene. To this mixture, 10.5 g (0.15 mol) of finely-divided particles of potassium methylate was gradually added at room temperature in a stream of a nitrogen gas. After the addition of the potassium methylate, this mixture was stirred for 2 hours, with the temperature of the reaction mixture maintained at 30° to 40° C. The thus prepared reaction mixture was diluted with 200 ml of water and extracted with toluene. After this extract was dried, a portion of the toluene was removed therefrom. The extract was subjected to column chromatography using silica gel as a carrier and toluene/n-hexane as an eluting solution and recrystallized from the mixture of toluene and n-hexane with the mixture ratio of 1:1, whereby 12. 5 g of the polyolefin derivative No. 23 having the following formula was obtained in a 39% yield. The melting point of the product was 159.5° to 160.5° C.

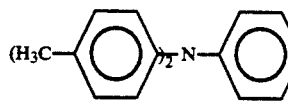

The results of the elemental analysis of the thus obtained polyolefin derivative No. 23 were as follows:

|  | % C | % H | % N |
|---|---|---|---|
| Calculated | 88.42 | 7.10 | 4.48 |
| Found | 88.33 | 7.02 | 4.47 |

The above calculation was based on the formula for polyolefin derivative No. 23 of $C_{46}H_{44}N_2$.

SYNTHESIS EXAMPLES 2 through 14

Synthesis Example 1 was repeated except that 4-(N,N-di-p-tolylamino)benzaldehyde was replaced by the aldehyde compounds No. 2 to No. 14 as shown in the following Table 1, whereby polyolefin derivatives according to the present invention were obtained.

TABLE 1

| Synthesis Example No. | Aldehyde Compound | Polyolefin Derivative | Melting Point (°C.) (Recrystallization Solvent) | Results of Elemental Analysis (%) Found/Calculated | | |
|---|---|---|---|---|---|---|
| | | | | C | H | N |
| 2 | 9-anthracenecarboxaldehyde | bis(2-(9-anthryl)vinyl) structure | 177.0~178.0 (Toluene/n-hexane) | 93.95/93.97 | 6.04/6.03 | — |
| 3 | 4-(dibenzylamino)benzaldehyde | corresponding bis-styryl derivative | 144.5~146.5 (Toluene/n-hexane) | 88.39/88.42 | 7.08/7.10 | 4.47/4.48 |
| 4 | 4-(diphenylamino)benzaldehyde | corresponding bis-styryl derivative | 138.0~139.0 (Toluene/n-hexane) | 88.40/88.45 | 6.53/6.52 | 5.01/5.03 |
| 5 | 4-[N-phenyl-N-(3-methoxyphenyl)amino]benzaldehyde | corresponding bis-styryl derivative | 153.5~154.5 (Toluene/n-hexane) | 84.22/84.04 | 6.50/6.41 | 4.20/4.46 |
| 6 | 9-ethyl-3-carbazolecarboxaldehyde | corresponding bis-styryl derivative | 124.0~126.0 (Toluene/n-hexane) | 87.10/87.14 | 6.85/6.88 | 5.92/5.98 |
| 7 | 10-ethyl-3-phenothiazinecarboxaldehyde | corresponding bis-styryl derivative | 163.5~164.5 (Toluene/n-hexane) | 76.58/76.65 | 6.08/6.05 | 5.23/5.26 |
| 8 | 4-(diethylamino)benzaldehyde | corresponding bis-styryl derivative | Oily | 82.88/82.92 | 9.65/9.64 | 7.41/7.44 |

TABLE 1-continued
| Synthesis Example No. | Aldehyde Compound | Polyolefin Derivative | Melting Point (°C.) (Recrystallization Solvent) | Results of Elemental Analysis (%) Found/Calculated | | |
|---|---|---|---|---|---|---|
| | | | | C | H | N |
| 9 |  | 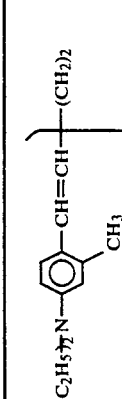 | Oily | 83.11/83.11 | 9.98/9.96 | 6.87/6.92 |
| 10 |  | 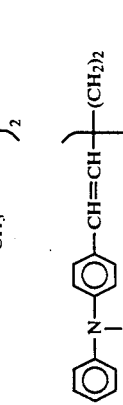 | 86.0~87.0 (Toluene/n-hexane) | 86.40/86.44 | 7.21/7.26 | 6.30/6.30 |
| 11 |  |  | 183.0~184.0 | 87.67/87.83 | 8.55/8.64 | 3.57/3.53 |
| 12 |  | 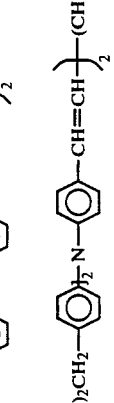 | Waxy | 87.98/87.83 | 8.59/8.64 | 3.51/3.53 |
| 13 |  | 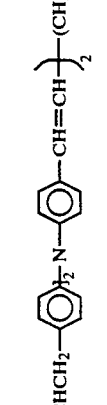 | 52.0~53.0 | 87.72/87.83 | 8.70/8.64 | 3.58/3.53 |
| 14 | 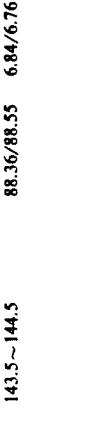 |  | 143.5~144.5 | 88.36/88.55 | 6.84/6.76 | 4.66/4.69 |

SYNTHESIS EXAMPLE 15

A mixture of 19.2 g (0.025 mol) of hexamethylene-1,6-bis(triphenylphosphonium)dibromide and 15.8 g (0.053 mol) of 4-(N,N-di-p-tolylamino)benzaldehyde was dissolved in 150 ml of toluene. To this mixture, 5.3 g (0.075 mol) of finely-divided particles of potassium methylate was gradually added at room temperature in a stream of a nitrogen gas. After the addition of the potassium methylate, this mixture was stirred for 1 hour, with the temperature of the reaction mixture maintained at 40° to 45° C. The thus prepared reaction mixture was diluted with 100 ml of water and extracted with toluene. After this extract was dried, a portion of the toluene was removed therefrom. The extract was subjected to column chromatography using silica gel as a carrier and toluene/n-hexane as an eluting solution and recrystallized from the mixed solvent of methanol and toluene, whereby 8.6 g of the polyolefin derivative No. 93 having the following formula was obtained in a 52.4% yield. The melting point of the product was 118.5° to 120.0° C.

The results of the elemental analysis of the thus obtained polyolefin derivative No. 93 were as follows:

|  | % C | % H | % N |
|---|---|---|---|
| Calculated | 88.30 | 7.41 | 4.29 |
| Found | 88.26 | 7.35 | 4.23 |

The above calculation was based on the formula for polyolefin derivative No. 93 of $C_{48}H_{48}N_2$.

An ultraviolet absorption spectrum of the above synthesized polyolefin derivative No. 93, measured in a dichloromethane solvent, indicates the following peaks:
$\lambda_1$: 308 nm
$\lambda_2$: 258 nm

SYNTHESIS EXAMPLES 16 through 24

Polyolefin derivatives (diene compounds wherein R=H, N=0 in formula I) as shown in the following Table 2 were obtained in the same manner as in Synthesis Example 15.

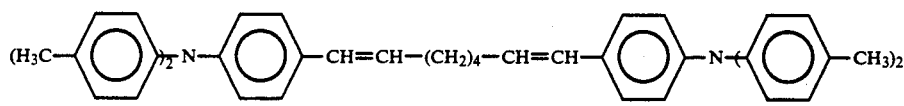

TABLE 2

| Synthesis Example No. | Polyolefin Derivative (Formula I wherein R = H and n = 0) A | m | Maximum Peak Visible · Ultraviolet Absorption Spectrum (in Dichloro Methane Solvent) (nm) | Melting Point (°C.) (Recrstallization Solvent) | Results of Elemental Analysis (%) Found/Calculated C | H | N |
|---|---|---|---|---|---|---|---|
| 16 | —⟨◯⟩—N⟨⟨◯⟩⟩₂ | 3 | $\lambda_1$: 308 $\lambda_2$: 238 | 45.0~47.0 (Toluene/n-hexane) | /  88.60/88.62 | 6.49/6.57 | 4.80/4.81 |
| 17 | —⟨◯⟩—N⟨⟨◯⟩⟩₂ | 4 | $\lambda_1$: 308 $\lambda_2$: 288 | 118.5~120.0 (Methanol/Toluene) | 88.48/88.55 | 6.72/6.76 | 4.65/4.69 |
| 18 | —⟨◯⟩—N⟨⟨◯⟩⟩₂ | 8 | $\lambda_1$: 312 $\lambda_2$: 236 | 93.5~94.5 (Toluene/n-hexane) | 88.25/88.30 | 7.50/7.41 | 4.20/4.29 |
| 19 | —⟨◯⟩—N⟨⟨◯⟩—CH₃⟩₂ | 3 | $\lambda_1$: 310 $\lambda_2$: 238 | 55.5~57.5 (Toluene/n-hexane) | 88.32/88.36 | 7.26/7.26 | 4.35/4.38 |
| 20 | —⟨◯⟩—N⟨⟨◯⟩—CH₃⟩₂ | 8 | $\lambda_1$: 314 $\lambda_2$: 236 | 93.5~94.0 (Toluene/n-hexane) | 88.07/88.09 | 7.89/7.96 | 3.90/3.95 |
| 21 | —⟨◯⟩—N⟨CH₂—⟨◯⟩⟩₂ | 3 | 296 | Oily | 88.35/88.36 | 7.31/7.26 | 4.35/4.38 |
| 22 | —⟨◯⟩—N⟨CH₂—⟨◯⟩⟩₂ | 4 | 292 | 85.0~88.0 (Methanol/Toluene) | 88.33/88.30 | 7.40/7.41 | 4.26/4.29 |

TABLE 2-continued

| Synthesis Example No. | Polyolefin Derivative (Formula I wherein R = H and n = 0) A | m | Maximum Peak Visible · Ultraviolet Absorption Spectrum (in Dichloro Methane Solvent) (nm) | Melting Point (°C.) (Recrstallization Solvent) | Results of Elemental Analysis (%) Found/Calculated | | |
|---|---|---|---|---|---|---|---|
| | | | | | C | H | N |
| 23 | —⟨◯⟩—N⫶CH₂—⟨◯⟩⫶₂ | 8 | 292 | Oily | 88.00/88.09 | 7.82/7.96 | 3.89/3.95 |
| 24 | [carbazole with C₂H₅ on N, 9-substituted] | 3 | λ₁: 280 λ₂: 242 | Oily | 87.02/87.09 | 7.13/7.11 | 5.90/5.80 |

In the photoconductor according to the present invention, at least one polyolefin derivative having the formula (I) is contained in the photoconductive layer 2a, 2b, 2c, 2d and 2e. The polyolefin derivatives can be employed in different ways, for example, as shown in FIG. 1, FIG. 2, FIG. 3, FIG. 4 and FIG. 5.

In the photoconductor as shown in FIG. 1, a photoconductive layer 2a is formed on an electroconductive support 1, which photoconductive layer 2a comprises a polyolefin derivative, a sensitizing dye and a binder agent (binder resin). In this photoconductor, the polyolefin derivative works as a photoconductive material, through which charge carriers which are necessary for the light decay of the photoconductor are generated and transported. However, the polyolefin derivative itself scarcely absorbs light in the visible light range and, therefore, it is necessary to add a sensitizing dye which absorbs light in the visible light range in order to form latent electrostatic images by use of visible light.

Figure 2:
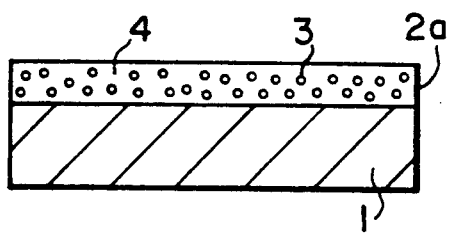

In the photoconductor as shown in FIG. 2, a photoconductive layer 2b is formed on an electroconductive support 1, which photoconductive layer 2b comprising a charge generating material 3 dispersed in a charge transporting medium 4 comprising a polyolefin derivative and a binder agent. In this embodiment, the polyolefin derivative and the binder agent or the mixture of a binder agent and a plasticizer) constitute the charge transporting medium 4 in combination. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the polyolefin derivative not overlap in the visible light range. This is because, in order that the charge generating material 3 produce charge carriers efficiently, it is necessary that light pass through the charge transporting medium 4 and reach the surface of the charge generating material 3. Since the polyolefin derivative having the above-described general formula (I) do not substantially absorb light in the visible range, they can work effectively as charge transporting materials in combination with the charge generating material 3 which absorbs the light in the visible region and generates charge carriers.

Figure 3:
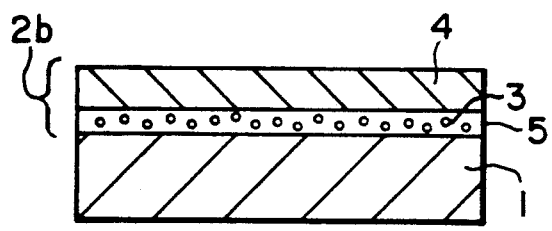

In the photoconductor as shown in FIG. 3, there is formed on the electroconductive support 1 a two-layered photoconductive layer 2c comprising a charge generation layer 5 consisting essentially of the charge generating material 3, and a charge transport layer 4 containing a polyolefin derivative.

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the polyolefin derivative mainly works for transporting charge carriers. The generation and transportation of the charge carriers are performed by the same mechanism as that in the photoconductor shown in FIG. 2.

Figure 4:
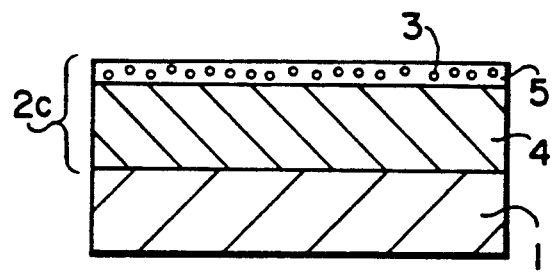

In the photoconductor as shown in FIG. 4, the overlaying order of the charge generation layer 5 and the charge transport layer 4 containing the polyolefin derivative is reversed as compared with the electrophotographic photoconductor as shown in FIG. 3. The mechanism of the generation and transportation of charge carriers is substantially the same as that of the photoconductor shown in FIG. 3.

Figure 5:
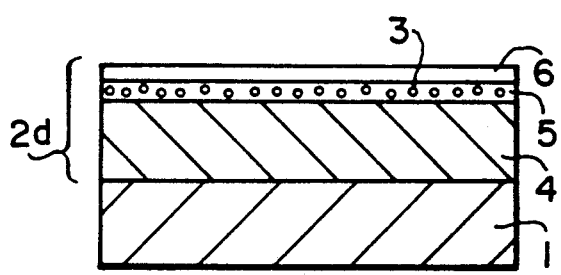

In the above photoconductor, a protective layer 6 may be formed on the charge generation layer 5 as shown in FIG. 5 for protecting the charge generation layer 5 from the viewpoint of mechanical strength.

When an electrophotographic photoconductor according to the present invention as shown in FIG. 1 is prepared, at least one polyolefin derivative having the previously described formula (I) is dissolved in a binder resin solution, and a sensitizing dye is then added to the above-prepared mixture, so that a photoconductive layer coating liquid is prepared. The thus prepared photoconductive layer coating liquid is coated on an electroconductive support 1 and dried, so that a photoconductive layer 2a is formed on the electroconductive support 1.

It is preferable that the thickness of the photoconductive layer 2a be in the range of 3 to 50 μm, more preferably in the range of 5 to 20 μm. It is preferable that the amount of the polyolefin derivative contained in the photoconductive layer 2a be in the range of 30 to 70 wt. %, more preferably about 50 wt. % of the total weight of the photoconductive layer 2a. Further, it is preferable that the amount of the sensitizing dye contained in the photoconductive layer 2a be in the range of 0.1 to 5 wt. %, more preferably in the range of 0.5 to 3 wt. % of the total weight of the photoconductive layer 2a.

As the sensitizing dye, the following can be employed in the present invention: triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes, such as cyanin; and pyrylium dyes, such as 2,6-diphenyl-4-(N,N-dimethylaminophenyl)thiapyrylium perchlorate and benzopyrylium salts (Japanese Patent Publication 48-25658). These sensitizing dyes can be used alone or in combination.

An electrophotogrpahic photoconductor according to the present invention as shown in FIG. 2 can be prepared, for example, by the following method. A charge generating material 3 in the form of finely-divided particles is dispersed in a solution in which one or more polyolefin derivatives and a binder agent are dispersed. The thus prepared dispersion is coated on the electroconductive support 1 and then dried, whereby a photoconductive layer 2b is formed on the electroconductive support 1.

It is preferable that the thickness of the photoconductive layer 2b be in the range of 3 to 50 μm, more preferably in the range of 5 to 20 μm. It is preferable that the amount of the polyolefin derivative contained in the photoconductive layer 2b be in the range of 10 to 95 wt. %, more preferably in the range of 30 to 90 wt. % of the total weight of the photoconductive layer 2b. Further, it is preferable that the amount of the charge generating material 3 contained in the photoconductive layer 2b be in the range of 0.1 to 50 wt. %, more preferably in the range of 1 to 20 wt. % of the total weight of the photoconductive layer 2b.

Specific examples of the charge generating material 3 are as follows: inorganic pigments, such as selenium, a selenium tellurium alloy, cadmium sulfide, a cadmium sulfide - selenium alloy, and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); azo pigments having a carbazole skeleton (Japanese Laid-Open Patent Application 53-95033), azo pigments having a distyrylbenzene skeleton (Japanese Laid-Open Patent Application 53-133445), azo pigments having a triphenylamine skeleton (Japanese Laid-Open Patent Application 53-132347), azo pigments having a dibenzothiophene skeleton (Japanese Laid-Open Patent Application 54-21728), azo pigments having an oxazole skeleton (Japanese Laid-Open Patent Application 54-12742), azo pigments having a fluorenone skeleton (Japanese Laid-Open Patent Application 54-22834), azo pigments having a bisstilbene skeleton (Japanese Laid-Open Patent Application 54-17733), azo pigments having a distyryl oxadiazole skeleton (Japanese Laid-Open Patent Application 54-2129), azo pigments having a distyryl carbazole skeleton (Japanese Laid-Open Patent Application 54-14967); phthalocyanine-type pigments such as C.I. Pigment Blue 16 (C.I. 74100); indigo-type pigments such as C.I. Vat Brown 5 (C.I. 73410) and C.I. Vat Dye (C.I. 73030); and perylene-type pigments, such as algo Scarlet B and Indanthrene Scarlet R (made by Bayer Co., Ltd.). These charge generating materials can be used alone or in combination.

An electrophotographic photoconductor according to the present invention as shown in FIG. 3 can be prepared, for example, by the following method. A charge generating material 3 is vacuum-evaporated on the electroconductive support 1, whereby a charge generation layer 5 is formed. Alternatively, a charge generating material 3 in the form of finely-divided particles is dispersed in a solution of a binder agent, and this dispersion is applied to the electroconductive support 1 and then dried. If necessary, the applied layer is subjected to buffing to make the surface smooth or to adjust the thickness of the layer to a predetermined thickness, whereby a charge generation layer 5 is formed. A charge transport layer 4 is then formed on the above-prepared charge generation layer 5 by applying a solution of one or more polyolefin derivatives and a binder agent to the charge generation layer 5 and then drying the applied solution. In this photoconductor, the charge generating material employed is the same as that employed in the photoconductor shown in FIG. 2.

It is preferable that the thickness of the charge generation layer 5 be 5 μm or less, more preferably 2 μm or less. It is preferable that the thickness of the charge transport layer 4 be in the range of 3 to 50 μm, more preferably in the range of 5 to 20 μm.

In the case where the charge generation layer 5 is prepared by coating the dispersion in which finely-divided particles of a charge generating material 3 are dispersed in a binder agent on the electroconductive support 1, it is preferable that the amount of the charge generating material in the charge generation layer 5 be in the range of 10 to 95 wt. %, more preferably in the range of 50 to 90 wt. % of the entire weight of the charge generation layer 5. Further, it is preferable that the amount of the polyolefin derivative contained in the charge transport layer 4 be in the range of 10 to 95 wt. %, more preferably in the range of 30 to 90 wt. % of the entire weight of the charge transport layer 4.

The electrophotographic photoconductor as shown in FIG. 4 can be prepared, for example, by coating a solution of a polyolefin derivative and a binder agent on the electroconductive support 1 and drying the same to form a charge transport layer 4. Then, on the above-prepared charge transport layer 4, a dispersion of finely-divided charge generating material particles, with addition thereto of a binder agent when necessary, is coated by spray coating and dried, so that a charge generation layer 5 is formed on the charge transport layer 4. The thickness of each of the two layers 4 and 5 and the compositions thereof may be the same as those of the photoconductive layer 2c in the photoconductor shown in FIG. 3.

When a protective layer 6 is formed on the charge generation layer 5 by coating an appropriate resinous solution by the spray coating method, the photoconductor as shown in FIG. 5 can be prepared.

As the electroconductive support 1 for use in the present invention, a metal plate or metal foil, for example, made of aluminum, a plastic film on which a metal, for example, aluminum is evaporated, or paper which has been treated so as to be electroconductive, can be employed.

As the binder agent for use in the present invention, condensation resins, such as polyamide, polyurethane, polyester, epoxy resin, polyketone and polycarbonate; and vinyl polymers such as polyvinylketone, polystyrene, poly-N-vinylcarbazole and polyacrylamide, can be used. These resins can also be employed as a resin component in the above-mentioned protective layer 6.

Other conventional electrically insulating and adhesive resins can also be used as the binder agent in the present invention. When necessary, there can be added to the binder resins a plasticizer, for example, halogenated paraffin, polybiphenyl chloride dimethylnaphthalene and dibutyl phthalate.

In the above-described photoconductors according to the present invention, if necessary, an adhesive or barrier layer can be interposed between the electroconductive support and the photoconductive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE 1

The following components were ground and dispersed in a ball mill to prepare a charge generation layer coating liquid:

| | Parts by Weight |
|---|---|
| Diane Blue (C.I. Pigment Blue) 25, C.I. 21180 | 76 |

| | Parts by Weight |
|---|---|
| 2% tetrahydrofuran solution of a polyester resin (Trademark "Vylon 200" made by Toyobo Co., Ltd.) | 1,260 |
| Tetrahydrofuran | 3,700 |

This charge generation layer coating liquid was coated by a doctor blade on the aluminum-deposited surface of an aluminum-deposited polyester base film, which served as an electroconductive support, so that a charge generation layer was formed on the electroconductive support with a thickness of about 1 μm when dried at room temperature.

Then the following components were mixed and dissolved, so that a charge transport layer coating liquid was prepared:

| | Parts by Weight |
|---|---|
| Polyolefin derivative No. 23 | 2 |
| Polycarbonate resin (Trademark) "Panlite K 1300" made by Teijin Limited.) | 2 |
| Tetrahydrofuran | 16 |

The thus prepared charge transport layer coating liquid was coated on the aforementioned charge generation layer by a doctor blade and dried at 80° C. for 2 minutes and then at 105° C. for 5 minutes, so that a charge transport layer with a thickness of about 20 μm was formed on the charge generation layer. Thus, an electrophotographic photoconductor No. 1 according to the present invention was prepared.

EXAMPLES 2 THROUGH 72

Example 1 was repeated except that the charge generating material and the polyolefin derivative working as the charge transporting material employed in Example 1 were respectively replaced by the charge generating materials and the polyolefin derivatives as listed in Table 3 and Table 4, whereby electrophotographic photoconductors No. 2 through No. 72 according to the present invention were prepared.

TABLE 3

| Photoconductor No. | Charge Generating Material | Charge Transporting Material (Polyolefin Derivative No.) |
|---|---|---|
| 1 | [structure: Ph-HNOC, OH, H₃CO, OCH₃, HO, CONH-Ph with -N=N- linkages] | 23 |
| 2 | [structure: Ph-HNOC, OH, Cl, Cl, HO, CONH-Ph with -N=N- linkages] | 23 |

TABLE 3-continued
| Photo-conductor No. | Charge Generating Material | Charge Transporting Material (Polyolefin Derivative No.) |
|---|---|---|
| 3 | 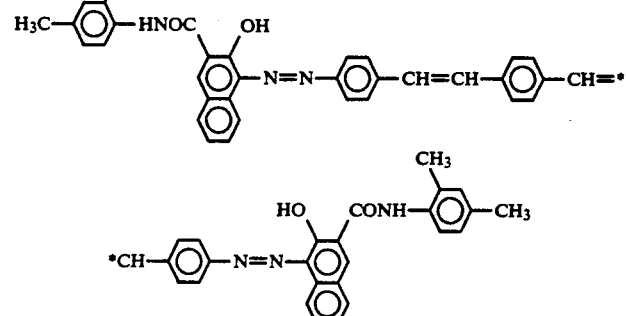<br>(hereinafter referred to as P-1) | 23 |
| 4 | 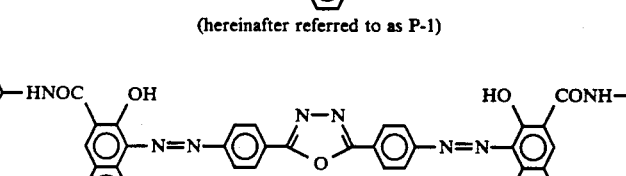 | 23 |
| 5 | 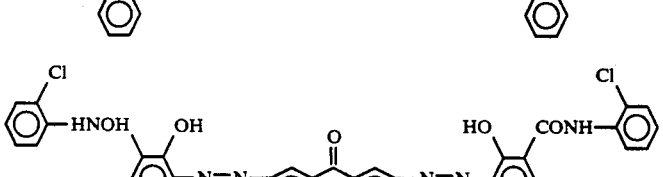<br>(hereinafter referred to as P-2) | 23 |
| 6 | 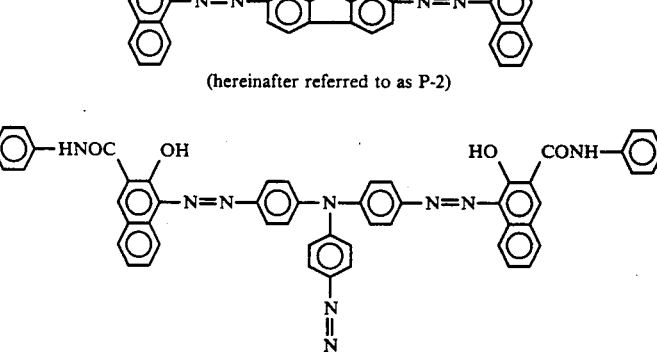 | 23 |
| 7 | β-type Copper Phthalocyanine | 23 |
| 8 | 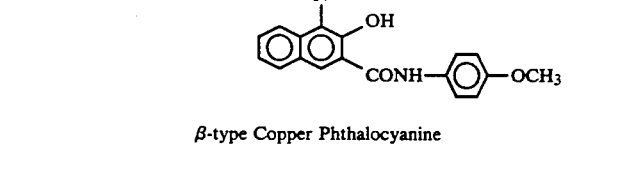 | 22 |
| 9 | 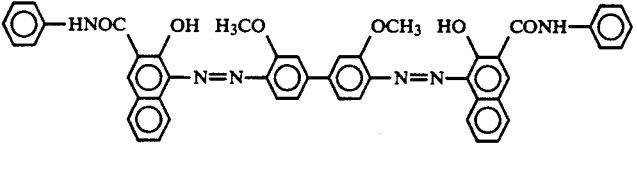 | 22 |
| 10 | P-1 | 22 |
| 11 | P-2 | 22 |

TABLE 3-continued

| Photo-conductor No. | Charge Generating Material | Charge Transporting Material (Polyolefin Derivative No.) |
|---|---|---|
| 12 | P-1 | 2 |
| 13 | P-2 | 2 |
| 14 | P-1 | 10 |
| 15 | P-2 | 10 |
| 16 | P-1 | 19 |
| 17 | P-2 | 19 |
| 18 | P-1 | 26 |
| 19 | P-2 | 26 |
| 20 | P-1 | 24 |
| 21 | P-2 | 24 |
| 22 | P-1 | 25 |
| 23 | P-2 | 25 |
| 24 | P-1 | 41 |
| 25 | P-2 | 41 |
| 26 | P-1 | 46 |
| 27 | P-2 | 46 |
| 28 | P-1 | 40 |
| 29 | P-2 | 40 |
| 30 | P-1 | 49 |
| 31 | P-2 | 49 |
| 32 | P-1 | 50 |
| 33 | P-2 | 50 |
| 34 | P-1 | 52 |
| 35 | P-2 | 52 |
| 36 | P-1 | 55 |
| 37 | P-2 | 55 |
| 38 | P-1 | 57 |
| 39 | P-2 | 57 |
| 40 | P-1 | 60 |
| 41 | P-2 | 60 |
| 42 | P-1 | 61 |
| 43 | P-2 | 61 |
| 44 | P-1 | 62 |
| 45 | P-2 | 62 |

TABLE 4

| Photo-conductor No. | Charge Generating Material | Charge Transporting Material (Polyolefin Derivative No.) |
|---|---|---|
| 46 | [Ph-HNOC, OH, H3CO, OCH3, HO, CONH-Ph; linked by N=N to biphenyl with two naphthalene groups] | 93 |
| 47 | [Ph-HNOC, OH, Cl, Cl, HO, CONH-Ph; linked by N=N to dichlorobiphenyl with two naphthalene groups] | 93 |
| 48 | [H3C, H3C-phenyl-HNOC, OH, naphthalene-N=N-phenyl-CH=CH-phenyl-CH=*] | 93 |

TABLE 4-continued

| Photo-conductor No. | Charge Generating Material | Charge Transporting Material (Polyolefin Derivative No.) |
|---|---|---|
| | (structure, hereinafter referred to as P-1) | |
| 49 | (structure) | 93 |
| 50 | (structure, hereinafter referred to as P-2) | 93 |
| 51 | (structure) | 93 |
| 52 | β-type Copper Phthalocyanine | 31 |
| 53 | (structure) | 92 |
| 54 | (structure) | 30 |
| 55 | P-1 | 92 |
| 56 | P-2 | 92 |
| 57 | P-1 | 86 |
| 58 | P-2 | 86 |
| 59 | P-1 | 80 |
| 60 | P-2 | 80 |
| 61 | P-1 | 87 |
| 62 | P-2 | 87 |
| 63 | P-1 | 81 |
| 64 | P-2 | 81 |
| 65 | P-1 | 82 |

TABLE 4-continued

| Photo-conductor No. | Charge Generating Material | Charge Transporting Material (Polyolefin Derivative No.) |
|---|---|---|
| 66 | P-2 | 82 |
| 67 | P-1 | 91 |
| 68 | P-2 | 91 |
| 69 | P-1 | 97 |
| 70 | P-2 | 97 |
| 71 | P-1 | 64 |
| 72 | P-2 | 64 |

EXAMPLE 73

Selenium was vacuum-deposited with a thickness of about 1.0 μm on an about 300 μm thick aluminum plate so that a charge generation layer was formed on the aluminum plate.

A charge transport layer coating liquid was prepared by mixing and dispersing the following components:

| | Parts by Weight |
|---|---|
| Polyolefin derivative No. 23 | 2 |
| Polyester resin (Trademark "Polyester Adhesive 49000" made by Du Pont Co.) | 3 |
| Tetrahydrofuran | 45 |

The thus prepared charge transport layer coating liquid was coated on the above-prepared selenium-deposited charge generation layer by a doctor blade, dried at room temperature and further dried under reduced pressure, so that a charge transport layer with a thickness of about 10 μm was formed on the charge generation layer. Thus an electrophotographic photoconductor No. 73 according to the present invention was prepared.

EXAMPLE 74

Example 73 was repeated except that selenium-deposited charge generation layer with a thickness of about 1.0 μm was replaced by a charge generation layer comprising a perylene pigment having the following formula with a thickness of about 0.6 μm, whereby an electrophotographic photoconductor No. 74 was prepared.

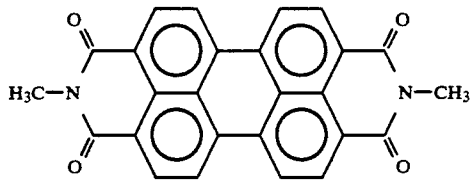

EXAMPLE 75

A mixture of 1 part by weight of Diane Blue (the same as employed in Example 1) and 158 parts by weight of tetrahydrofuran was ground and dispersed in a ball mill. To this mixture, 12 parts by weight of the polyolefin derivative No. 23 and 18 parts by weight of a polyester resin (Trademark "Polyester Adhesive 49000" made by Du Pont Co.) were added and mixed, whereby a photoconductive layer coating liquid was prepared.

The thus prepared photoconductive layer coating liquid was coated on an aluminum-deposited polyester film by a doctor blade and dried at 100° C. for 30 minutes, so that a photoconductive layer with a thickness of about 16 μm was formed on the aluminum-deposited polyester film. Thus an electrophotographic photoconductor No. 75 according to the present invention was prepared.

EXAMPLE 76

The same charge transport layer coating liquid as employed in Example 1 was coated by a doctor blade on the aluminum-deposited polyester base film and dried at room temperature, so that a charge transport layer having a thickness of about 20 μm was formed on the electroconductive support.

Then the following components were ground and dispersed in a ball mill to prepare a dispersion:

| | Parts by Weight |
|---|---|
| Bisazo pigment (p-2) | 13.5 |
| Polyvinyl butyral (Trademark "XYHL" made by Union Carbide Plastic Co., Ltd.) | 5.4 |
| Tetrahydrofuran | 680.0 |
| Ethyl cellosolve | 1,020.0 |

To the above dispersion, 1,700 parts by weight of ethyl cellosolve were further added and the mixture was dispersed, whereby a charge generation layer coating liquid was prepared.

The thus prepared charge generation layer coating liquid was coated on the above-prepared charge transport layer by spray coating and dried at 100° C. for 10 minutes, whereby a charge generation layer having a thickness of about 0.2 μm was formed on the charge transport layer.

Then a methanol/n-buthanol solution of a polyamide resin (Trademark "CM-8000" made by Toray Industries, Inc.) was coated on the charge generation layer by spray coating and dried at 120° C. for 30 minutes, whereby a protective layer with a thickness of about 0.5 μm was formed on the charge generation layer. Thus an electrophotographic photoconductor No. 76 according to the present invention was prepared.

EXAMPLE 77

Selenium was vacuum-deposited with a thickness of about 1.0 μm on an about 300 μm thick aluminum plate, so that a charge generation layer was formed on the aluminum plate.

A charge transport layer coating liquid was prepared by mixing and dispersing the following components:

|  | Parts by Weight |
|---|---|
| Polyolefin derivative No. 93 | 2 |
| Polyester resin (Trademark "Polyester Adhesive 49000" made by Du Pont Co.) | 3 |
| Tetrahydrofuran | 45 |

The thus prepared charge transport layer coating liquid was coated on the above-prepared selenium-deposited charge generation layer by a doctor blade, dried at room temperature and further dried under reduced pressure, so that a charge thickness of about 10 μm was formed on the charge generation layer. Thus an electrophotogrpahic photoconductor No. 77 according to the present invention was prepared.

EXAMPLE 78

Example 77 was repeated except that selenium-deposited charge generation layer with a thickness of about 1.0 μm was replaced by a charge generation layer comprising a perylene pigment having the following formula with a thickness of about 0.6 um, and that the polyolefin derivative No. 93 was replaced by the polyolefin derivative No. 92 in the formulation of the charge transport layer coating liquid, whereby an electrophotographic photoconductor No. 78 was prepared.

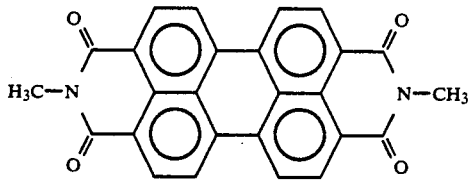

EXAMPLE 79

A mixture of 1 part by weight of Diane Blue (the same as employed in Example 46) and 158 parts by weight of tetrahydrofuran was ground and dispersed in a ball mill. To this mixture, 12 parts by weight of the polyolefin derivative No. 93 and 18 parts by weight of a polyester resin (Trademark "Polyester Adhesive 49000" made by Du Pont Co.) were added and mixed, whereby a photoconductive layer coating liquid was prepared.

The thus prepared photoconductive layer coating liquid was coated on an aluminum-deposited polyester film by a doctor blade and dried at 100° C. for 30 minutes, so that a photoconductive layer with a thickness of about 16 μm was formed on the aluminum-deposited polyester film. Thus an electrophotographic photoconductor No. 79 according to the present invention was prepared.

EXAMPLE 80

The same charge transport layer coating liquid as employed in Example 46 was coated by a doctor blade on the aluminum-deposited polyester base film in the same manner as employed in Example 46, and dried at room temperature, so that a charge transport layer having a thickness of about 20 μm was formed on the electroconductive support.

Then the following components were ground and dispersed in a ball mill to prepare a dispersion:

|  | Parts by Weight |
|---|---|
| Bisazo pigment (p-2) | 13.5 |
| Polyvinyl butyral (Trademark "XYHL" made by Union Carbide Plastic Co., Ltd.) | 5.4 |
| Tetrahydrofuran | 680.0 |
| Ethyl cellosolve | 1,020.0 |

To the above dispersion, 1,700 parts by weight of ethyl cellosolve were further added and the mixture was dispersed, whereby a charge generation layer coating liquid was prepared.

The thus prepared charge generation layer coating liquid was coated on the above-prepared charge transport layer by spray coating and dried at 100° C. for 10 minutes, whereby a charge generation layer having a thickness of about 0.2 μm was formed on the charge transport layer.

Then a methanol/n-buthanol solution of a polyamide resin (Trademark "CM-8000" made by Toray Industries, Inc.) was coated on the charge generation layer by spray coating and dried at 120° C. for 30 minutes, whereby a protective layer with a thickness of about 0.5 μm was formed on the charge generation layer. Thus an electrophotographic photoconductor No. 80 according to the present invention was prepared:

The thus prepared electrophotographic photoconductors No. 1 to No. 80 were charged negatively or positively in the dark under application $-6$ kV or $+6$ kV of corona charge for 20 seconds and then allowed to stand in the dark for 20 seconds without applying any charge thereto. At this moment, the surface potential $V_{po}$ (V) of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 4.5 lux, so that the exposure $E_{\frac{1}{2}}$ (lux·seconds) required to reduce the initial surface potential $V_{po}$ (V) to $\frac{1}{2}$ the initial surface potential $V_{po}$ (V) was measured. The results are shown in Table 5.

Each of the above electrophotographic photoconductors No. 1 through No. 80 was incorporated in a commercially available electrophotographic copying machine and a latent electrostatic image was formed thereon by being exposed to a light image. The latent electrostatic image was developed with a dry type developer to a visible toner image, electrostatically transferred to a transfer sheet made of plain paper and fixed thereto. As a result, a clear transferred image was obtained by each of the photoconductors. When a liquid developer was employed instead of the dry type developer, clear transfer images were obtained likewise.

TABLE 5

| Example No. | $V_{po}$ (V) | $E_{1/2}$ (lux · second) |
|---|---|---|
| 1 | $-1210$ | 1.10 |
| 2 | $-1045$ | 0.99 |
| 3 | $-1119$ | 0.97 |
| 4 | $-1320$ | 1.70 |
| 5 | $-1005$ | 0.93 |
| 6 | $-1210$ | 0.96 |
| 7 | $-1010$ | 1.21 |
| 8 | $-1220$ | 1.87 |
| 9 | $-1070$ | 1.90 |
| 10 | $-1130$ | 1.03 |

TABLE 5-continued

| Example No. | $V_{po}$ (V) | $E_{1/2}$ (lux · second) |
|---|---|---|
| 11 | −1100 | 1.13 |
| 12 | −1450 | 1.27 |
| 13 | −1260 | 1.93 |
| 14 | −1320 | 1.05 |
| 15 | −1190 | 1.21 |
| 16 | −1250 | 1.20 |
| 17 | −1130 | 1.41 |
| 18 | −1130 | 0.91 |
| 19 | −990 | 0.80 |
| 20 | −1190 | 1.00 |
| 21 | −1220 | 0.99 |
| 22 | −1320 | 0.98 |
| 23 | −1180 | 0.92 |
| 24 | −1220 | 0.92 |
| 25 | −1200 | 0.80 |
| 26 | −1320 | 0.98 |
| 27 | −1000 | 1.00 |
| 28 | −1190 | 0.99 |
| 29 | −1210 | 0.85 |
| 30 | −1180 | 1.20 |
| 31 | −1040 | 0.98 |
| 32 | −1370 | 1.08 |
| 33 | −1200 | 1.13 |
| 34 | −1190 | 0.78 |
| 35 | −1250 | 0.60 |
| 36 | −1310 | 1.50 |
| 37 | −1190 | 1.32 |
| 38 | −1210 | 1.00 |
| 39 | −1310 | 0.97 |
| 40 | −1700 | 2.96 |
| 41 | −1566 | 3.05 |
| 42 | −1497 | 4.30 |
| 43 | −1495 | 4.78 |
| 44 | −1320 | 4.78 |
| 45 | −1250 | 2.40 |
| 46 | −1350 | 1.85 |
| 47 | −1180 | 1.70 |
| 48 | −1320 | 1.06 |
| 49 | −1690 | 2.92 |
| 50 | −1240 | 1.10 |
| 51 | −1310 | 1.20 |
| 52 | −1180 | 2.00 |
| 53 | −1490 | 2.01 |
| 54 | −1100 | 1.99 |
| 55 | −1280 | 1.08 |
| 56 | −1160 | 1.00 |
| 57 | −1320 | 1.22 |
| 58 | −1180 | 1.31 |
| 59 | −1470 | 2.01 |
| 60 | −1600 | 2.23 |
| 61 | −1330 | 1.17 |
| 62 | −1370 | 1.36 |
| 63 | −1600 | 1.65 |
| 64 | −1640 | 3.84 |
| 65 | −1250 | 1.21 |
| 66 | −1320 | 1.40 |
| 67 | −1220 | 1.01 |
| 68 | −1310 | 1.21 |
| 69 | −1230 | 1.21 |
| 70 | −1470 | 1.10 |
| 71 | −1460 | 1.20 |
| 72 | −1310 | 1.71 |
| 73 | −1370 | 2.80 |
| 74 | −1290 | 2.50 |
| 75 | +1180 | 1.40 |
| 76 | +1040 | 0.78 |
| 77 | −1070 | 2.81 |
| 78 | −1490 | 4.31 |
| 79 | +1210 | 2.21 |
| 80 | +1380 | 1.21 |

What is claimed is:

1. Polyolefin derivative having the following formula (I):

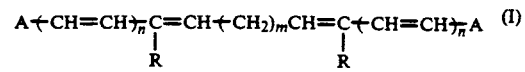

wherein A represents

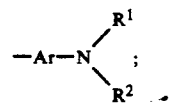

wherein Ar represents an arylene group or a divalent thiophene group of the formula

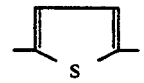

and $R^1$ represents an alkyl group, an aralkyl group or an aryl group, $R^2$ represents an aralkyl group or an aryl group, R represents hydrogen, alkyl group, an aralkyl group or an aryl group; m is an integer of 2 to 8; and n is an integer of 0 or 1.

2. A polyolefin derivative having the formula (I):

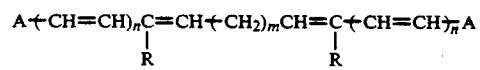

wherein A represents

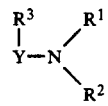 wherein Y is a phenylene group, n=0,
m=2,
R is hydrogen,
$R^1$ and $R^2$ each represent a phenyl group which may be substituted with a lower alkyl group or a lower alkoxy group and
$R^3$ represents hydrogen or a lower alkyl group.

3. A polyolefin derivative having the formula (I):

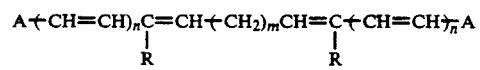

wherein A represents

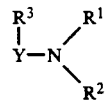

wherein Y is a phenylene group,
R is hydrogen,
n=0,
m=2,
$R^1$ and $R^2$ each represent a phenyl group which may be substituted with a methyl group or a methoxy group, and
$R^3$ is hydrogen or a methyl group.

4. A polyolefin derivative having the formula (I):

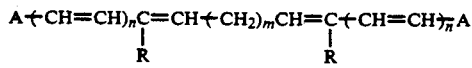

wherein A represents

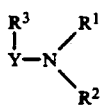

wherein Y is a naphthylene group, a bisphenylene group, or

wherein R¹ and R² each represent a lower alkyl group, a benzyl group or a phenyl group, R is hydrogen, N=0 and m is an integer of 2–8.

5. The polyolefin derivatives as claimed in claim 1, wherein n is 0.

6. The polyolefin derivative as claimed in claim 1, wherein A is

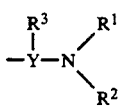

wherein Y is a phenylene group, a naphthylene group, a bisphenylene group, or

R¹ and R² each represent an alkyl group, an aralkyl group, or an aryl group; R³ represents hydrogen or a lower alkyl group; R represents hydrogen or a lower alkyl group; m is an integer of 2 to 8; and n is zero (0).

7. The polyolefin derivatives as claimed in claim 6, wherein Y represents a phenylyene group.

8. The polyolefin derivatives as claimed in claim 7, wherein R¹ represents a lower alkyl group, a benzyl group, or a phenyl group, R² represents an aralkyl group or an aryl group; R³ represents hydrogen or a lower alkyl group; R represents hydrogen or a lower alkyl group; and m is an integer of 2 to 8.

9. The polyolefin derivatives as claimed in claim 7, wherein R¹ represents a lower alkyl group, a benzyl group, or a phenyl group, R² represents an aralkyl group or an aryl group; R³ represents hydrogen or a lower alkyl group; R represents hydrogen or a lower alkyl group; and m is 2.

10. The polyolefin derivatives as claimed in claim 4, wherein R¹ and R² each represent a phenyl group which may be substituted with a lower alkyl group or a lower alkoxyl group; R represents hydrogen; and m is 2.

11. The polyolefin derivatives as claimed in claim 4, wherein R¹ and R² each represent a phenyl group which may be substituted with a methyl group or a methoxy group; R represents hydrogen; and m is 2.

12. A polyolefin derivative of the formula,

wherein M is an integer of 2–8
wherein A is selected from the group consisting of

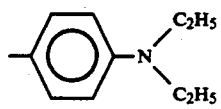

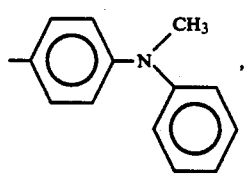

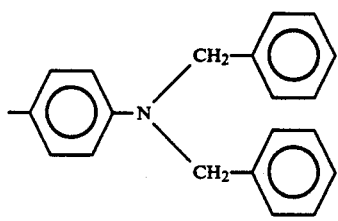

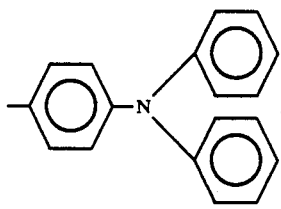

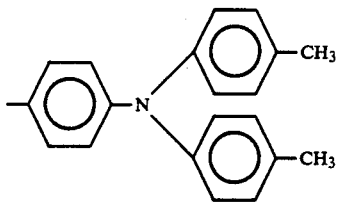

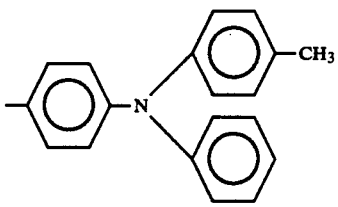

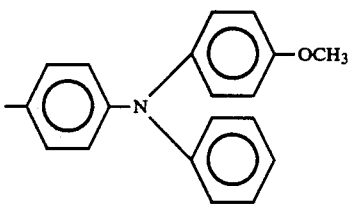

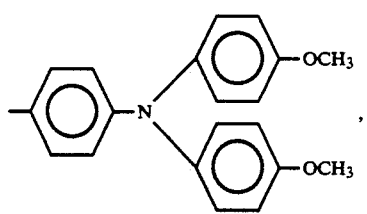,
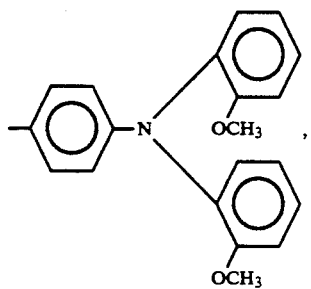,
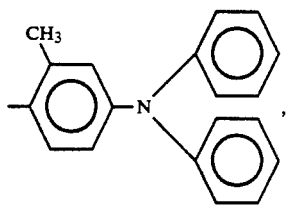,
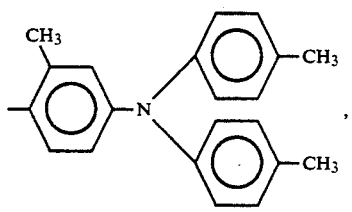,
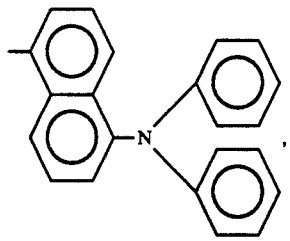,
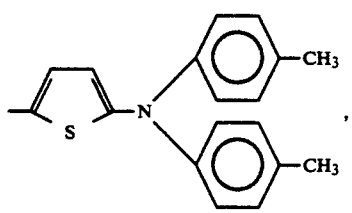,
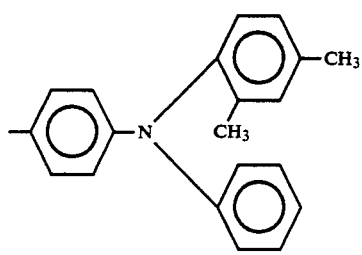
and
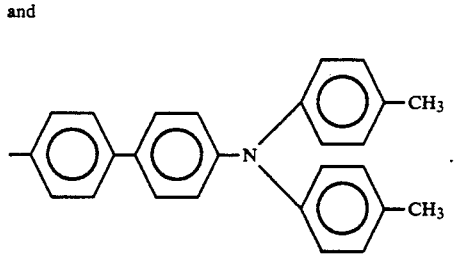
13. A polyolefin derivative selected from the group consisting of
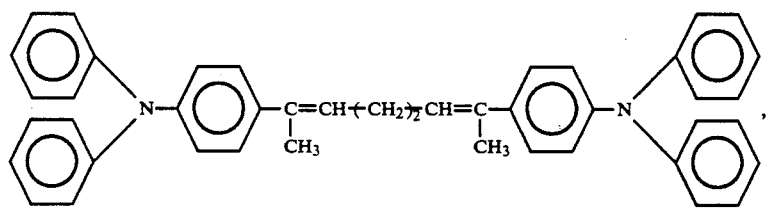,
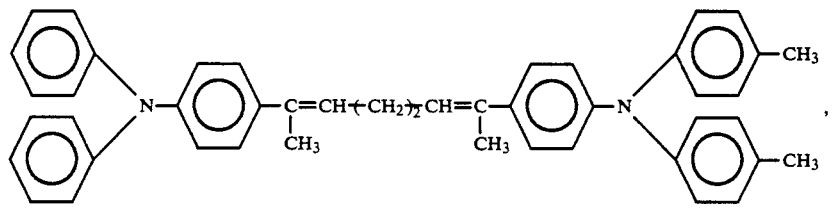,

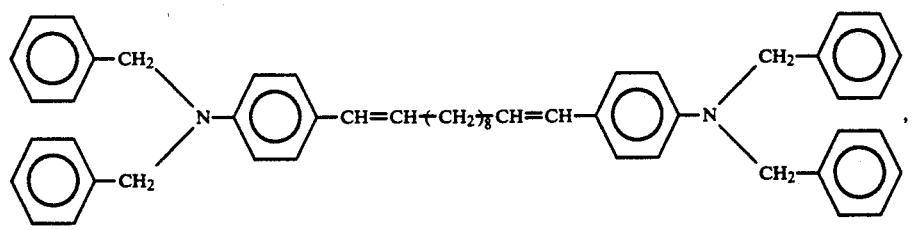
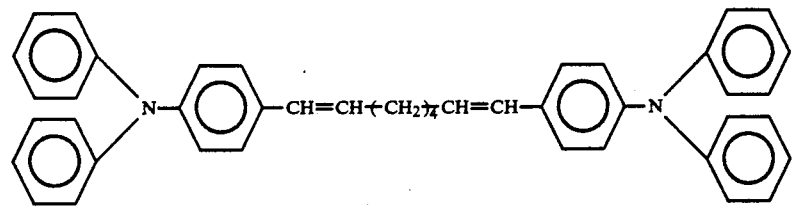
and
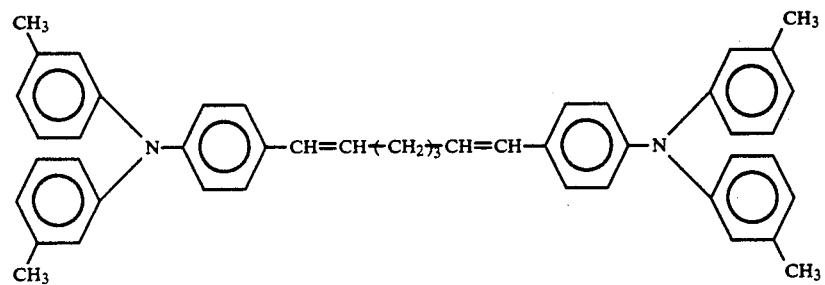

UNITED STATES PATENT AND TRADEMARK OFFICE
CERTIFICATE OF CORRECTION

PATENT NO. : 5,252,750
DATED : October 12, 1993
INVENTOR(S) : Mitsuru Hashimoto, et al It is certified that error appears in the above-indentified patent and that said Letters Patent is hereby corrected as shown below:

Column 59, Line 15, "a charge thickness of" should read --a charge transport layer with a thickness of--

Column 59, Line 17, "electrophotogrpahic" should read --electrophotographic--

Column 59, Line 26, "0.6 um" should read --0.6 $\mu$m--

Column 60, Line 29, "prepared:" should read --prepared.--

Column 60, Line 32, "under application -6kV" should read --under application of -6kV--

Column 64, Line 3, "A-CH=CH-(CH$_2$)MCH=CH-A" should read --A-CH=CH-(CH$_2$)$_m$CH Signed and Sealed this Twenty-seventh Day of December, 1994

Attest:

BRUCE LEHMAN

*Attesting Officer*    *Commissioner of Patents and Trademarks*